US00PP30698P2

(12) United States Plant Patent
Taquet

(10) Patent No.: US PP30,698 P2
(45) Date of Patent: Jul. 9, 2019

(54) ***PENSTEMON* PLANT NAMED 'BALMIBLAVBI'**

(50) Latin Name: ***Penstemon* hybrid**
Varietal Denomination: Balmiblavbi

(71) Applicant: Ball Horticultural Company, West Chicago, IL (US)

(72) Inventor: Valentin Taquet, Amsterdam (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,943

(22) Filed: Aug. 31, 2018

(51) Int. Cl.
*A01H 5/02* (2018.01)
*A01H 6/68* (2018.01)

(52) U.S. Cl.
USPC ..... Plt./465

(58) Field of Classification Search
USPC ..... Plt./263.1, 465
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Penstemon* plant named 'Balmiblavbi', characterized by its light lavender and white bi-colored flowers, dark green-colored foliage, and moderately vigorous, compact-upright growth habit, is disclosed.

1 Drawing Sheet

Latin name of genus and species of plant claimed: *Penstemon* hybrid.
Variety denomination: 'Balmiblavbi'.

BACKGROUND OF THE INVENTION

The present invention relates to a new and distinct cultivar of *Penstemon* plant botanically known as *Penstemon* hybrid and hereinafter referred to by the cultivar name 'Balmiblavbi'.

The new cultivar originated in a controlled breeding program in Hem, the Netherlands during August 2014. The objective of the breeding program was the development of *Penstemon* cultivars having a long flowering season with a compact-upright growth habit.

The new *Penstemon* cultivar is the result of cross-pollination. The female (seed) parent of the new cultivar is the proprietary *Penstemon* hybrid breeding selection coded G2312-01, not patented, characterized by its medium pink-colored flowers, dark green-colored foliage, and moderately vigorous, semi-upright growth habit. The male (pollen) parent of the new cultivar is the proprietary *Penstemon* hybrid breeding selection coded G2312-04, not patented, characterized by its light violet-colored flowers, dark green-colored foliage, and moderately vigorous, mounded growth habit. The new cultivar was discovered and selected as a single flowering plant within the progeny of the above stated cross-pollination during July 2015 in a controlled environment in Hem, the Netherlands.

Asexual reproduction of the new cultivar by terminal stem cuttings since July 2015 in Hem, the Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmiblavbi' as a new and distinct cultivar of *Penstemon* plant:

1. Light lavender and white bi-colored flowers;
2. Dark green-colored foliage; and
3. Moderately vigorous, compact-upright growth habit.

Plants of the new cultivar differ from plants of the female and male parents primarily in having a different flower color and a compact-upright growth habit.

Of the many commercially available *Penstemon* cultivars, the most similar in comparison to the new cultivar is QUARTZ Amethyst 'Novapename', U.S. Plant Pat. No. 27,821. However, in comparison, plants of the new cultivar differ from plants of 'Novapename' in at least the following characteristics:

1. Plants of the new cultivar have smaller sized flowers than plants of 'Novapename'; and
2. Plants of the new cultivar have an outer surface corolla tube color different from plants of 'Novapename'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balmiblavbi'. The plants were approximately five months old. The plants were grown in one-gallon containers for approximately 4 weeks in a greenhouse in Elburn, Ill. followed by approximately 12 weeks in an outdoor nursery in West Chicago, Ill. Plants were given two pinches, one at one week before transplant and one two weeks after transplant.

DETAILED BOTANICAL DESCRIPTION

Figure 1:
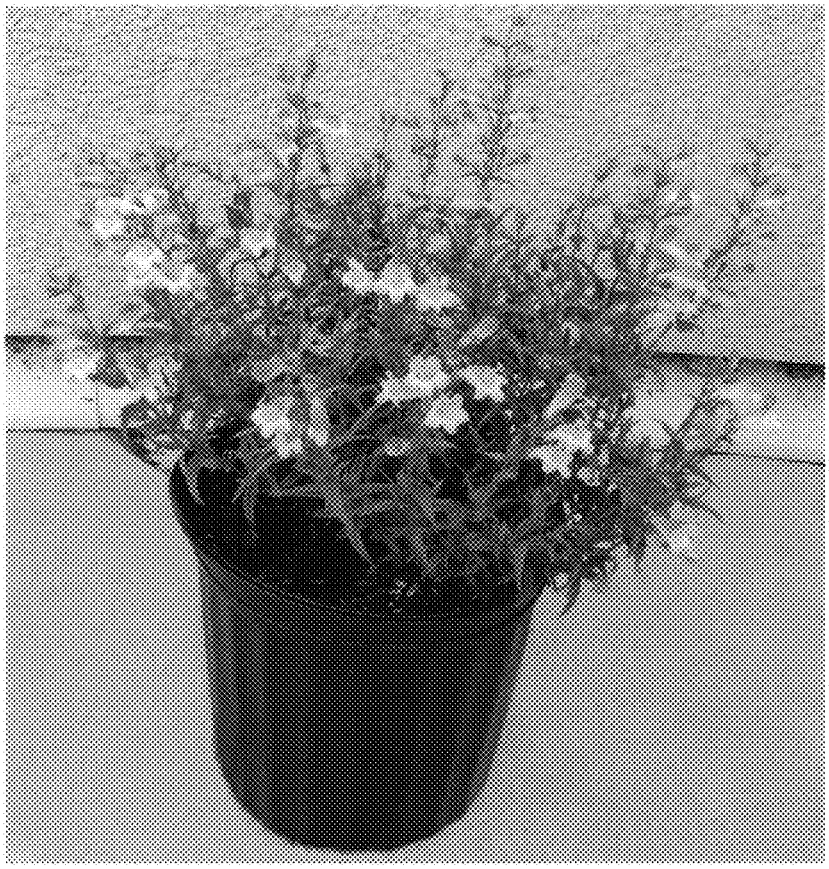
FIG. 1 illustrates a side view of the overall growth and flowering habit of 'Balmiblavbi'.
Figure 2:
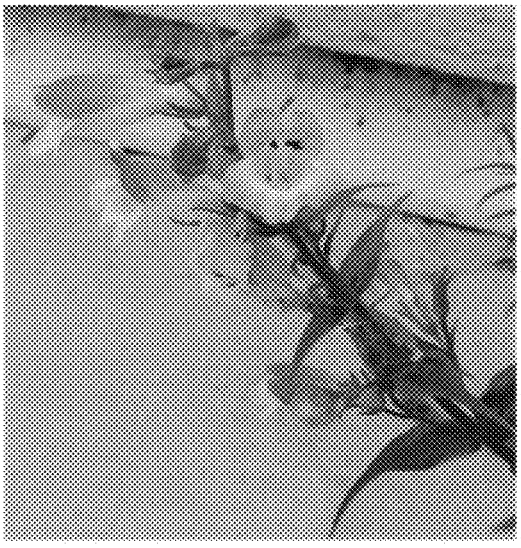
FIG. 2 illustrates a close-up view of an inflorescence of 'Balmiblavbi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2018 under natural light conditions in West Chicago, Ill. The following descriptions and measurements describe approximately five-month old plants produced from cuttings from stock plants and grown under conditions comparable to those used in commercial practice. The plants were grown in one-gallon containers for approximately 4 weeks in a greenhouse in Elburn, Ill. followed by approximately 12 weeks in an outdoor nursery in West Chicago, Ill. Plants were given two pinches, one at one week before transplant and one two weeks after transplant. Greenhouse temperatures in Elburn, Ill. were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Penstemon* hybrid 'Balmiblavbi'.

Parentage:

*Female parent*.—Proprietary *Penstemon* hybrid breeding selection coded G2312-01, not patented.

*Male parent*.—Proprietary *Penstemon* hybrid breeding selection coded G2312-04, not patented.

Propagation:

*Type cutting*.—Terminal stem.

*Time to initiate roots*.—Approximately 10 to 12 days.

*Time to produce a rooted cutting*.—Approximately 5 to 6 weeks.

*Root description*.—Fine to medium, fibrous white to light brown in color.

*Rooting habit*.—Freely branching.

Plant description:

*Commercial crop time*.—Approximately 10 to 12 weeks from a rooted cutting to finish in a 15 cm pot.

*Growth habit and general appearance*.—Tender perennial; moderately vigorous, compact-upright growth habit.

*Hardiness*.—USDA Zones 7a (0° F. to 5° F./−17.8° C. to −15° C.).

*Size*.—Height from soil level to top of plant plane: Approximately 30.0 cm. Width: Approximately 44.0 cm.

*Branching habit*.—Freely branching. Pinching enhances lateral branching. Quantity of branches per plant: Approximately 3 main basal branches and approximately 33 lateral branches.

*Lateral branch*.—Shape: Round in cross section. Strength: Strong. Length to base of peduncle: Approximately 18.0 cm. Diameter: Approximately 3.0 mm to 5.0 mm. Length of central internode: Approximately 1.5 cm. Texture: Densely pubescent with very short hairs. Color of young stem: 146C. Color of mature stem: 146C with an overlay of 187A.

Foliage description:

*General description*.—Quantity of leaves per branch: Approximately 18. Fragrance: None detected. Form: Simple. Arrangement: Opposite and decussate.

*Leaves*.—Aspect: Acute angle to stem with blade perpendicular and tips downward turning. Shape: Lanceolate. Margin: Shallowly serrate. Apex: Acute. Base: Sessile. Venation pattern: Pinnate. Length of mature leaf: Approximately 3.8 cm. Width of mature leaf: Approximately 8.0 mm. Texture of upper and lower surfaces: Glabrous. Color of upper surface of young and mature foliage: 137A with venation of 146D. Color of lower surface of young and mature foliage: Closest to 137B with venation of 146D.

Flowering description:

*Flowering habit*.—'Balmiblavbi' is freely flowering under outdoor growing conditions blooming in late spring and reblooming in late summer.

*Lastingness of individual floret*.—Approximately 6 to 7 days.

Inflorescence description:

*General description*.—Type: Terminal raceme, not persistent, multilateral arrangement. Quantity of open inflorescences per plant: Approximately 25. Fragrance: None detected. Length or height of inflorescence: Approximately 6.0 cm to 13.0 cm. Width of inflorescence: Approximately 3.5 cm to 5.5 cm. Quantity of fully-open flowers per inflorescence: Approximately 3 to 6.

*Peduncle*.—Strength: Strong. Aspect: Erect. Length: Approximately 2.5 cm. Diameter: Approximately 2.0 mm. Texture: Densely glandular pubescent. Gland color: Colorless, transparent. Color: 146C tinted with 187A in sun.

Flower description:

*Type*.—Single, zygomorphic.

*Bud*.—Rate of opening: Generally takes 3 to 4 days for bud to progress from first color to fully open flower.

*Bud just before opening*.—Shape: Obovoid. Length: Approximately 1.4 cm. Diameter: Approximately 6.0 mm. Texture: Densely glandular pubescent. Gland color: Colorless, transparent. Color: Calyx of 146C; petals of 70A with NN155A.

*Corolla*.—Shape: Bilabiate, upper lip of two lobes and lower lip having three lobes. Width: Approximately 1.9 cm. Length: Approximately 1.8 cm. Depth: Approximately 2.5 cm.

*Upper lip lobes*.—Shape: Ovate. Margin: Entire. Apex: Rounded. Length from throat: Approximately 5.0 mm. Width: Approximately 5.0 mm. Texture of upper (inner) surface: Glabrous. Texture of lower (outer) surface: Sparsely glandular pubescent. Gland color: Colorless, transparent. Color of upper (inner) surface when first and fully open: NN155D with an underlay of N82B. Color of lower (outer) surface when first and fully open: N82A.

*Lower lip lobes*.—Shape: Ovate. Margin: Entire. Apex: Rounded. Length from throat of central lobe: Approximately 5.0 mm. Width of central lobe: Approximately 6.0 mm. Length from throat of lateral lobes: Approximately 6.0 mm. Width of lateral lobes: Approximately 7.0 mm. Texture of upper (inner) surface: Glabrous. Texture of lower (outer) surface: Sparsely glandular pubescent. Gland color: Colorless, transparent. Color of upper (inner) surface when first and fully open: NN155D with an underlay of N82B. Color of lower (outer) surface when first and fully open: NN155D and N82A to N82B.

*Corolla tube*.—Length: Approximately 1.9 cm. Width: Approximately 1.0 cm. Texture of inner surface: Glabrous. Texture of outer surface: Densely glandular pubescent. Gland color: Colorless, transparent. Color of inner surface: NN155A. Color of outer surface: NN155D with adaxial surface having a heavy overlay of 70A to 70B.

*Calyx*.—Shape: Cupped. Length: Approximately 1.0 cm. Diameter: Approximately 1.0 cm.

*Sepals*.—Quantity per flower: 5. Shape: Lanceolate. Apex: Acute. Base: Truncate. Length: Approximately 1.0 cm. Width: Approximately 1.0 mm. Texture of inner surface: Glabrous. Texture of outer surface: Densely glandular pubescent. Gland color: Colorless, transparent. Color of inner surface: 146C. Color of outer surface: 146D.

*Pedicel*.—Strength: Strong, flexible. Aspect: At an acute angle. Length: Approximately 1.0 cm. Diameter: Approximately 1.0 mm. Texture: Densely glandular pubescent. Gland color: Colorless, transparent. Color: 146D tinted with 187A.

*Reproductive organs*.—Androecium: Stamen quantity: 5 per flower, one lacking an anther and having dense pubescence on tip. Stamen length: Approximately 1.8 to 2.0 cm. Filament length: Approximately 1.7 to 1.9. Filament length of fixed portion: Approximately 7.0 mm. Filament color: NN155D. Anther shape: Horseshoe-like. Anther length: Approximately 2.0 mm. Anther color: NN155A lightly tinted with N82A. Pollen amount: Abundant. Pollen color: NN155D. Gynoecium: Pistil quantity: 1 per flower. Pistil length: Approximately 2.0 cm. Stigma shape: Conical. Stigma length: Less than 1.0 mm. Stigma color: NN155D. Style length: Approximately 1.6 cm. Style color: NN155D. Ovary length: Approximately 4.0 mm. Ovary color: N144C.

Seed and fruit production: Neither seed nor fruit production has been observed.

Disease and pest resistance: Resistance to pathogens and pests common to *Penstemon* has not been observed.

What is claimed is:

1. A new and distinct cultivar of *Penstemon* plant named 'Balmiblavbi', substantially as herein illustrated and described.

* * * * *